(12) United States Patent
Burke

(10) Patent No.: US 9,347,074 B1
(45) Date of Patent: May 24, 2016

(54) BIOMASS PRETREATMENT WITH AMMONIUM BICARBONATE / CARBONATE EXPANSION PROCESS

(76) Inventor: Dennis Anthony Burke, Olympia, WA (US)

( * ) Notice: Subject to any disclaimer, the term of this patent is extended or adjusted under 35 U.S.C. 154(b) by 314 days.

(21) Appl. No.: 13/506,249

(22) Filed: Apr. 6, 2012

Related U.S. Application Data

(60) Provisional application No. 61/516,710, filed on Apr. 7, 2011.

(51) Int. Cl.
| | | |
|---|---|---|
| *C12Q 1/00* | (2006.01) | |
| *C12P 7/00* | (2006.01) | |
| *C12P 7/06* | (2006.01) | |
| *C12P 7/08* | (2006.01) | |
| *C12P 7/10* | (2006.01) | |
| *C08H 8/00* | (2010.01) | |

(52) U.S. Cl.
CPC ... *C12P 7/06* (2013.01); *C08H 8/00* (2013.01); *C12P 7/00* (2013.01); *C12P 7/08* (2013.01); *C12P 7/10* (2013.01); *C12Q 1/00* (2013.01)

(58) Field of Classification Search
CPC ............ C12P 19/02; C12P 7/10; C12P 19/14; C12P 2201/00; C12P 7/54
See application file for complete search history.

(56) References Cited

U.S. PATENT DOCUMENTS

| | | | | |
|---|---|---|---|---|
| 4,329,320 A | * | 5/1982 | Vydra et al. | ........................ 423/1 |
| 4,356,196 A | * | 10/1982 | Hultquist | ........................ 426/69 |
| 4,600,590 A | | 7/1986 | Dale | |
| 5,037,663 A | | 8/1991 | Dale | |
| 5,171,592 A | * | 12/1992 | Holtzapple et al. | ............. 426/69 |
| 5,473,061 A | | 12/1995 | Bredereck et al. | |
| 7,806,957 B1 | | 10/2010 | Burke | |
| 7,811,455 B2 | | 10/2010 | Burke | |
| 7,915,017 B2 | | 3/2011 | Dale | |
| 2008/0182305 A1 | * | 7/2008 | Foody et al. | ................... 435/140 |
| 2009/0305372 A1 | * | 12/2009 | Hendriks | ...................... 435/161 |
| 2010/0267999 A1 | | 10/2010 | Lau et al. | |

OTHER PUBLICATIONS

"Slurry" in Oxford Dictionary of Chemistry, 6th Ed., 2008, Oxford University Press, 1 page.*
Wyman, C. E., et al., Comparative sugar recovery and fermentation data following pretreatment of poplar wood by leading technologies, Biotechnol. Prog. 2009, vol. 25, No. 2.
(Continued)

*Primary Examiner* — Sharmila G. Landau
*Assistant Examiner* — Sheridan MaCauley
(74) *Attorney, Agent, or Firm* — Brian J. Coyne

(57) ABSTRACT

A simple, inexpensive, and benign process to pretreat lignocellulose biomass for the economical production of biofuel and extraction of organic chemicals. Lignocellulose solids are mixed or blended with ammonium bicarbonate/carbonate and heated within a pressure reactor. At elevated temperature (e.g., >35° C.), the ammonium bicarbonate/carbonate dissociates into ammonia and carbon dioxide gases and water vapor, thereby causing a rise in pressure within the pressure reactor. Rapid release of the gases from the pressure reactor then ruptures biomass cell wall structures, which facilitates conversion of the cellulose and hemicellulose in the pretreated biomass to sugars that are fermentable into ethanol or other liquid fuels. Optionally, ammonia bicarbonate/carbonate can be reconstituted by cooling and precipitating the carbon dioxide and ammonia gases released from the pressure reactor for further use in the pretreatment process or sequestered as an end product.

28 Claims, 5 Drawing Sheets

ABFX Pretreatment Process Diagram

(56) References Cited

OTHER PUBLICATIONS

Kumar, D. and G.S. Murthy, Pretreatments and enzymatic hydrolysis of grass straws for ethanol production in the Pacific Northwest U.S., Biol. Engr. 3(2): 97-110.

MacLean, H.L., et al., The contribution of enzymes and process chemicals to the life cycle of ethanol, Environ. Res.Lett. 4(2009)(014001).

Sousa, L. et al., 'Cradle-to-grave' assessment of existing lignocellulose pretreatment technologies, Current Opinion in Biotech, 2009, 20:1-9.

Lynd, L.R. et al., How biotech can transform biofuels, Nature Biotechnology, vol. 26(2): 169-172 (Feb. 2008).

Mosier, N. et al., Features of promising technologies for pre-treatment of lignocellosic biomass, Bioresour. Technol., 96(6) 673-686.

* cited by examiner

ABFX Pretreatment Process Diagram

High Solids Digestion

Separate Fiber Digestion

Fiber Re-Digestion

Liquid Fuel Production

BIOMASS PRETREATMENT WITH AMMONIUM BICARBONATE / CARBONATE EXPANSION PROCESS

CROSS REFERENCE TO RELATED APPLICATIONS

This application claims the benefit of provisional application No. 61/516,710 by the same applicant for the same invention, filed on Apr. 7, 2011, entitled, "Ammonium Bicarbonate Expansion Process," the disclosure of which is incorporated herein.

STATEMENT REGARDING GOVERNMENT RESEARCH

The process was demonstrated under the National Science Foundation Small Business Innovative Research (SBIR) Phase 1: Economic Feasibility of the ABFX Process, Proposal Number 1142318.

BACKGROUND OF THE INVENTION

1. Field of Invention

This invention is an economical method for pretreating lignocellulosic biomass for the production of liquid and gaseous biofuels. "Biomass," as that term is used herein, includes any plant matter, plant residual, or waste substrate containing lignin, cellulose or hemicellulose.

2. Background Art

Plant cell walls are comprised of cellulose, hemicellulose and lignin, and collectively these compounds are called "lignocellulose." The production of biofuels from lignocellulosic biomass follows the pathway of 1) size reduction, 2) pretreatment to increase susceptibility to hydrolytic enzymes, 3) hydrolysis and fermentation, 4) extraction and recovery. The first step in biofuel production after size reduction is pretreatment wherein the biomass fibers are broken apart from the lignin structure to expose the cellulose and hemicellulose, destroy the cellulose crystalline structure and thereby produce degradable amorphous cellulose and hemicellulose. All lignocellulose pretreatments can be divided into four main categories:

1) Physical methods, including extrusion, dry milling (chipping, ball milling, and grinding), wet milling, irradiation, microwave, and swelling reagents (e.g., $ZnCl_2$);
2) Chemical methods, including dilute acids (dilute $H_2SO_4$, $H_3PO_4$, HCl, acetic acid, formic acid/HCl), alkalis (NaOH, lime, ammonia, amine), organosolv, oxidizing agents ($O_3$, NO, $H_2O_2$, $NaClO_2$), cellulose solvents (cadoxen), DMAc/LiCl, and concentrated $H_2SO_4$;
3) Physiochemical methods, including steam explosion with or without catalysts, $CO_2$ explosion, ammonia fiber explosion or expansion (AFEX), hot water with flow-through, supercritical fluid extractions ($CO_2$, $CO_2/H_2O$, $CO_2/SO_2$, $NH_3$, $H_2O$); and
4) Biological methods such as white rot fungi.

A number of hybrid systems have been proposed utilizing two or more of the categories described above.

The next step following pretreatment is hydrolysis through the use of enzymes, and/or hydrolytic organisms such as *Saccharomyces cerevisiae* or *Z. mobilis* to convert the cellulose and hemicellulose to sugars that can be fermented to ethanol. Pretreatment processes normally improve the enzymatic hydrolysis rates by several hundred percent. For example, the hydrolysis yield ($Y_h$=Glucose in Sample/Estimated Potential Glucose) of grass without pretreatment was <20% in 48 hours compared to 80% with hot water, or dilute acid, or dilute alkali pretreatment over the same period (Kumar and Murthy 2011). As stated above, a large variety of pretreatment technologies exist. The common technologies are hot water, dilute acid, aqueous ammonia soaking, wet oxidation, sulfur dioxide steam explosion, alkali soaking, and ammonia fiber explosion.

Although significant benefits are accrued through the use of pretreatment, the cost of pretreatment represents 30% to 40% of the cost of lignocellulosic ethanol production. The recalcitrance of the lignocellulosic substrate impacts the cost of pretreatment and downstream processes involving lignocellulose conversion to fuel. Pretreatment methods are thus strongly associated with downstream costs, including the enzymatic hydrolysis rate, enzyme loading, power consumption for mixing, product concentration, detoxification if inhibitors are generated, product purification, power generation, waste treatment demands, and other process variables. Starch-based grain or corn ethanol production uses the most economical pretreatment process, namely high-pressure hot water (pressure cooker) pretreatment. Other technologies for lignocellulosic pretreatment are more expensive since chemicals such as ammonia, concentrated or dilute acids, caustics such as lime or sodium hydroxide must be purchased. If acids are used, the treated biomass must be detoxified through a separate treatment step.

One of the most effective pretreatment technologies is ammonia fiber explosion (AFEX) where liquid ammonia and water are added to the dry biomass substrate under pressure, heated in a pressure reactor for a short duration of time (5 minutes±), and exploded through a rapid release of pressure resulting in the vaporization of the ammonia and the disintegration of the fibers (U.S. Pat. Nos. 3,707,436; 4,600,590; 5,171,592). Ninety to 95% of the ammonium can be recovered through a variety of subsequent process steps. Many studies and U.S. patents have focused on Ammonia Fiber Explosion since it is one of the most promising pretreatment techniques that least affect downstream cost and performance. Its use has been analyzed for the pretreatment of a variety of crop residues, grains, and both soft and hard woods. The primary disadvantage of the process, however, has been the high capital and operating cost associated with capturing and recycling ammonia. A brief history of its evolution follows:

In 1967, James J. O'Connor culminated his research on a new method for producing wood pulp that included the steps of impregnating a mass of lignocellulose chips with anhydrous ammonia, heating without the use of added steam within a closed reactor under pressure, and then suddenly releasing the pressure to cause the explosive removal of ammonia and the deformation and disintegration of the wood chips to a fibrous condition in which "the fibers were flexible, kinked, twisted, and curled." O'Connor had observed that "nitrogenous agents such as ammonia and amine-nitrogen compounds that have an —$NH_2$ group, for example, effectively swell and plasticize wood (O'Connor 1971). Twenty years later, Dale applied for and received a patent on "a method for increasing the reactivity and digestibility of cellulose with ammonia" (Dale 1986). The method was described as follows: "The cellulose is contacted, in a pressure vessel, with a volatile liquid swelling agent having a vapor pressure greater than atmospheric at ambient temperatures, such as ammonia. The contact is maintained for a sufficient time to enable said agent to swell the cellulose fibers. The pressure is rapidly reduced to atmospheric, allowing said agent to boil and explode the cellulose fiber structure. The rapid pressure reduction also causes some freezing of the cellulose. The agent is separated from said cellulose and recovered for recycling." The process was subsequently referred to as "Ammonia Freeze Explosion."

In 1987, Norman published a paper on the transformations of organic matter solubilized by anhydrous ammonia (Norman et al., 1987). Norman had observed that anhydrous ammonia solubilized the majority of the organic matter in soil and made such organic matter available for bacterial consumption and the subsequent release as carbon dioxide.

A summary of other patents and patent applications that followed are presented below.

Patents issued to Dale, U.S. Pat. Nos. 4,600,590 and 5,037,663, describe the use of various volatile chemical agents to treat the cellulose containing materials, particularly ammonia by what came to be known as the AFEX process (ammonia freeze or ammonia fiber explosion).

U.S. Pat. No. 5,171,592, issued to Holtzapple et al. (1992), provides an AFEX process in which the biomass is treated with liquid ammonia or any other appropriate swelling agent, exploded, and the swelling agent and the treated biomass are recovered.

U.S. Pat. No. 5,366,558 issued to Brink disclosed a process that uses two stages to hydrolyze the hemicellulose sugars and the cellulosic sugars in a countercurrent reactor.

U.S. Pat. No. 5,188,673 employs concentrated acid hydrolysis, which has the benefit of high conversion of biomass, but suffers from low product yields due to degradation and the requirement of acid recovery and recycle. Sulphuric acid concentrations used are 30-70 weight percent at temperatures less than 100° C.

U.S. Pat. No. 5,473,061 issued to Bredereck et al. (1995) describes a process which involves bringing the cellulose in contact with liquid ammonia at a pressure higher than atmospheric pressure in a pressure vessel and subsequent expansion by rapid reduction of the pressure to atmospheric pressure to activate the cellulose for subsequent chemical reactions.

U.S. patent application US 2007/0031918A1 by Dunson et al. provides a process in which the biomass at relatively high concentration is treated with relatively low concentration of ammonia relative to the dry weight of the biomass. The ammonia-treated biomass is then digested with a saccharification enzyme to produce fermentable sugars. The process utilizes vacuum for better ammonia penetration and recovery; it also uses a plasticizer for softening.

U.S. patent application US 2008/0008783A1 by Bruce Dale et al. disclosed a pretreatment process using concentrated ammonium hydroxide under pressure to improve the accessibility/digestibility of the polysaccharides from a cellulosic biomass. It also uses a combination of anhydrous ammonia and concentrated ammonium hydroxide solutions.

In December 2009, Dale applied for a U.S. patent for the separation of proteins from grasses utilizing the ammonia fiber explosion process (Dale et al., 2009). The process was described as: "A process for extracting an aqueous ammonium hydroxide solution from a plant biomass after an Ammonia Fiber Explosion (AFEX) process step is described. The proteins can be separated before or after a hydrolysis of sugar precursors (carbohydrates) from the biomass to produce sugars for fermentation to produce ethanol. The proteins are useful as animal feeds because of their amino acid food values."

In September 2009, Zhang applied for a U.S. patent on a highbrid, dilute-acid process that provides a novel method for conversion of plant material, including material containing cellulose, hemicellulose, and lignocellulose, to usable energy sources, such as carbohydrates, ethanol, and hydrogen (Zhang 2009). In general, the invention provides a novel lignocellulosic pretreatment by use of concentrated acid and cellulose solvents.

In March 2010, Geros applied for U.S. patent for a pretreatment process that involved sequestering of ammonia nitrogen following fermentation through the addition of acid (Geros 2010).

In September 2010, Kreisler applied for a US patent on a complex process for conditioning biomass using the steps of 1) flash dessicating the biomass to reduce a particle size of the biomass; 2) mixing the biomass with a liquid carrier; and 3) exposing the biomass and the liquid carrier to a mechanical hydrodynamic cavitation process (Kreisler 2010).

In October 2010, Parekh submitted a patent application for a process utilizing microorganisms, such as a *Clostridium* strain, in several stages to produce a final, fermented end product (Parekh 2010).

In December 2010, Sudhakaran applied for a US patent on a multistep process and system for the separation of biomass components into individual components such as cellulose, hemicellulose and lignin. The invention provides a process for separating lignin in its native form (Sudhakaran and Samuel 2010).

Over the past several years, an equally significant number of publications dealing with biomass pretreatment have been published in a variety of journals and books. In 2005, Mosier published a review describing the features of biomass pretreatment technologies (Mosier et al. 2005). Dale recently published research findings on the parameters controlling ammonia fiber explosion for the enzymatic hydrolysis of corn stover (Teymouri et al. 2005.). Sousa, et al., recently published an informative review and assessment of lignocellulosic pretreatment technologies (Sousa et al. 2009).

In spite of a number of investigations to optimize the Ammonia Fiber Explosion process it remains a complex process that requires considerable energy to heat and pressurize the water, ammonia, and biomass. The process is complicated by the ammonia recovery step. Ammonia provides two important advantages for use in this process. First, ammonia reacts with and solubilizes the organic substrate. Second, ammonia is volatile at low temperatures and thus can be easily expelled from the pretreated biomass in a gaseous state and subsequently recovered through a complex process.

$E^3$ Recent Research

Over the years the present inventor, doing business as $E^3$ Environmental Energy & Engineering Co., has conducted extensive research into high solids anaerobic digestion of a variety of substrates and the removal and recovery of ammonia nitrogen from anaerobic digestate, where the term "high solids" is here defined to mean a solids influent composition comprising at least 15 percent solids (w/v). He recently received U.S. Pat. No. 7,806,957 for his process for anaerobic digestion of high solids to produce balanced fertilizer and U.S. Pat. No. 7,811,455 for his method for recovery of ammonia nitrogen therefrom. He recently demonstrated the profitable removal and recovery of ammonia from liquid anaerobic digestate. The process recovered ammonium bicarbonate and carbonate as a liquid or solid product from the stripped ammonia while producing biomethane gas. The process used no chemicals and very little power to recover the ammonia. The recovered ammonia was then combined with $CO_2$ from the anaerobic digester's biogas, thereby producing biomethane fuel and ammonium bicarbonate/carbonate (U.S. patent application Ser. No. 13/373,860).

During the ammonia recovery research described above, he investigated the kinetics of ammonium bicarbonate solids precipitation with biogas $CO_2$ and stripped ammonia condensate. The experiments were carried out using various concentrations of liquid ammonium bicarbonate condensate obtained through the digestate ammonia stripping process. The ammonia condensate ($NH_4+H_2O$) was injected into 1 L Tedlar bags filled with $CO_2$. The condensate collapsed the bags while forming ammonium bicarbonate solids in an exothermic reaction. During a side experiment, the collapsed bags containing the ammonium bicarbonate solids were briefly (seconds) placed in a microwave, vaporizing the solids and refilling the bag with $CO_2$, $NH_3$, and $H_2O$. Upon removal of the bags from the microwave, the bags collapsed while the ammonium bicarbonate returned to the solid form. A small amount of external energy caused work to be performed through gas expansion (PV), and the removal of the bag to ambient temperature conditions resulted in an exothermic reaction, releasing energy and forming an ammonium bicarbonate precipitate from the $CO_2$, $NH_3$, and $H_2O$ in the bag. The cycle was repeated many times.

SUMMARY OF THE INVENTION

As a result of the preliminary work described above, $E^3$ applied for a U.S. provisional patent (Application No. 61/516,710) for a process that significantly reduces the energy required while simplifying the AFEX process. The process uses the ammonium bicarbonate (ABC) or ammonium carbonate solids precipitated from the ammonia recovery process described above or obtained from a separate source. A variety of solid ammonia nitrogen chemicals can be used in the ABFX process. They include ammonium bicarbonate ($NH_4HCO_3$), ammonium carbonate (($NH_4)_2CO_3$), ammonium carbamate ($NH_2COONH_4$), and Urea (($NH_2)_2CO$). The most advantageous compound or compounds are those that have the lowest melting or decomposition points. Ammonium bicarbonate has the lowest melting point of 41.9° C., followed by ammonium carbonate at 58° C. and ammonium carbamate at 59.61° C. Urea has a much higher melting point of 133° C. Any of the low melting point compounds may be used.

The process has been called the ABFX process since solid Ammonium Bicarbonate/carbonate is used rather than liquid or gaseous ammonia. In the ABFX process, the ammonium bicarbonate/carbonate solids are blended with the biomass at ambient pressure and temperature. The blended solids are then delivered to a pressure vessel at ambient pressure and temperature. The pressure vessel is then isolated (valve closed), and heated by a heat pump, microwave, or other heat source. Heating to temperatures of 40° C. to 60° C. vaporizes the ammonium bicarbonate/carbonate thus pressurizing the reactor and releasing the ammonia, water, and $CO_2$ vapors. Each mole (79 g) of ammonium bicarbonate will produce 67 L of gas that pressurizes the vessel. The pressure is then released after a predetermined reaction period. The released ammonia, carbon dioxide, and water vapor are then cooled to ambient temperatures by natural or artificial means such as the chiller side of the heat pump. Upon cooling, the gas vapors precipitate to form solid ammonium bicarbonate/carbonate at ambient temperatures. The ABC solids are then blended with the influent biomass again, and so on. FIG. 1 presents a schematic of the ABFX process.

The process simply requires a solids conveyor or pump, pressure reactor, gas cooling/(ABC) precipitation vessel and a heat pump to chill the precipitation vessel and heat the pressure reactor. The process bypasses the traditional liquid stage and high pressure pumping of liquid ammonia, biomass, and water. Energy consumption for moving gas under ambient conditions is considerably less than heating, cooling and pumping liquid under high pressure conditions. Depending on the ammonium bicarbonate to biomass feed ratios and the reactor compaction density, pressures exceeding 1,000 psi can be achieved by simply heating the reactor and vaporizing the ammonium bicarbonate at temperatures 100° C., more or less.

The amount of gases retained in the pressure vessel will be proportional to reactor void space or compaction density. Those retained gases can be cleared through the use of a flushing or carrier gas to conserve ammonia, $CO_2$, and $H_2O$ vapor. Some make-up $NH_3$, $CO_2$, $H_2O$ or $NH_4HCO_3$ may be required depending on the quantities retained by the pretreated biomass. Retention of $NH_3$, $CO_2$, $H_2O$ or $NH_4HCO_3$ can be minimized by operating the pressure reactor at high temperatures while using a low moisture content biomass feed. Any ammonia retained by the biomass will eventually be recovered in the patented ammonia recovery process following residual biomass treatment in a process such as anaerobic digestion.

Some of the water or $CO_2$ may be lost with the pretreated biomass, perhaps forming a weak carbonic acid that will aid in the biomass hydrolysis. However, at the elevated temperatures only small quantities of gas are expected to be dissolved in the water since Henry's constant varies with temperature. Little ammonia is expected to be lost given the elevated temperatures (>80° C.) and the volatility of ammonia. The lost water and perhaps $CO_2$ can be replenished by adding water vapor to the released gas or carrier gas. The ammonia recovery process can be integrated into the ABFX pretreatment process. Certainly, any ammonium bicarbonate lost with the pretreated biomass can be replaced through the ammonia recovery process following anaerobic digestion.

DETAILED DESCRIPTION OF THE INVENTION

Figure 1:
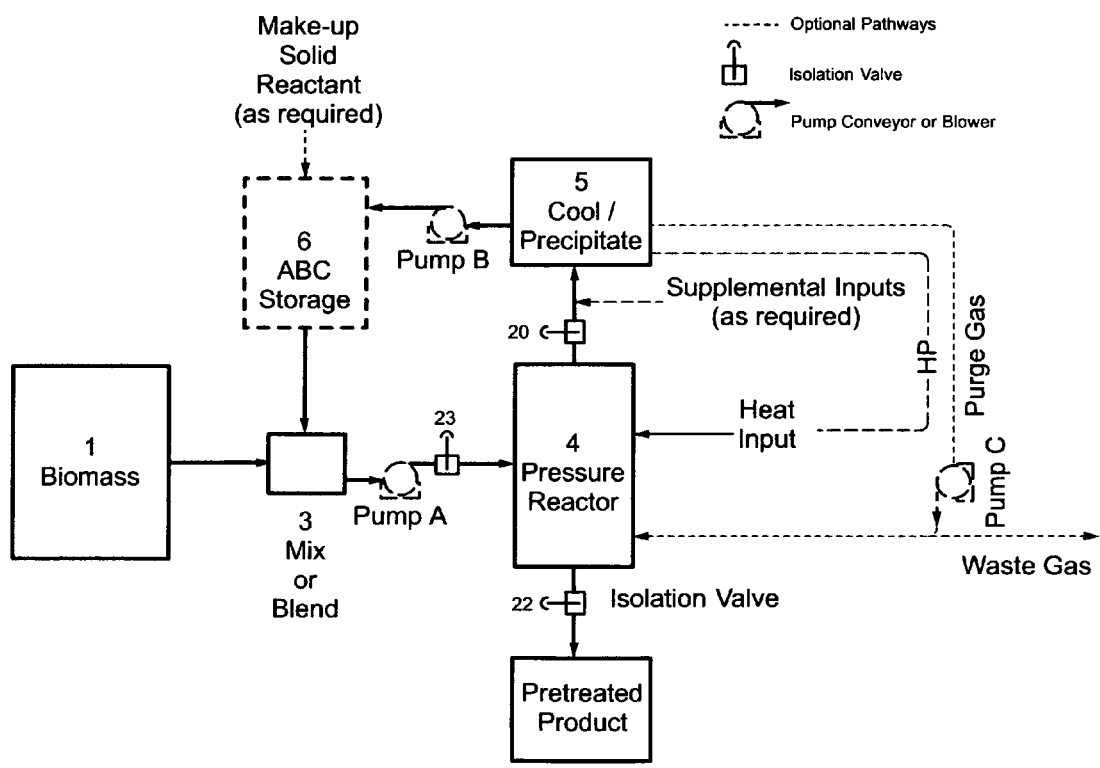
FIG. 1 is a schematic diagram of the ABFX pretreatment process of the present invention.

The object of this invention is to present an economical and efficient pretreatment process for a variety of substrates and biofuel processes. FIG. 1 presents a schematic diagram of the pretreatment process. The biomass 1 can be derived from a variety of plant and waste products as well as biofuel processes. The pretreatment process can be incorporated into high solids anaerobic digestion facilities, conventional anaerobic digestion facilities, and the digestion of residual solids resulting from other digestion or fermentation processes. The integration of the pretreatment process into those biofuel processes is presented in FIGS. 2-5, discussed below.

The biomass 1 can be macerated, ensilaged, or dried prior to pretreatment to store or improve the treatment process. A variety of preprocessing technologies may be beneficially utilized. The stored and/or preprocessed biomass 1 is then mixed and/or blended with ammonium bicarbonate and/or ammonium carbonate at any desired feed ratio to produce a blended and mixed biomass feedstock. The blending or mixing can take place in a mixing/blending vessel such as a separate reactor 3 or along a conveyor or within the influent hopper of a solids feed pump (e.g., Pump A in FIG. 1); alternatively, the mixing/blending vessel can be the pressure reactor vessel 4 itself, discussed below.

The mixed biomass and ABC reactant are delivered at ambient temperatures to a pressure reactor 4 by pump or conveyor. It is preferable to compact the mixed biomass feedstock into the pressure reactor to minimize void space. Upon filling the pressure reactor 4, pressure reactor isolation valves 20, 22, 23 are closed and the reactor 4 is heated to a temperature sufficient to decompose the ammonium carbonate and/or bicarbonate into gaseous ammonia, carbon dioxide and water vapor with concomitant increase in pressure within the reactor. The minimum temperature of decomposition will be between 35° and 60° C. The temperature, however, may be increased above those values and thereby increase the pressure within the pressure reactor 4. Reactor heating can be accomplished by any of a variety of means, such as solar, geothermal, or other renewable energy sources, engine waste heat, fuel combustion, heat pumps, or microwave radiation. A heat pump (HP) may provide the most economical heat source since cooling can be provided to the precipitation reactor 5 while heating the pressure reactor 4.

After heating, the pressure reactor 4 is held at the desired pressure and temperature for any desired time interval. The pressure achieved in the reactor 4 will be a function of the biomass to ABC reactant feed ratios, reactor void ratio, and temperature. After the desired holding time has passed, a first isolation valve 20 on the pressure reactor 4 can be opened to release the carbon dioxide, water vapor, and ammonia gases to a precipitation reactor 5 and residual contents of the pressure reactor ("Pretreated Product") can be removed therefrom by opening a second isolation valve 22. Any residual gases residing in the void spaces can be purged by recirculating a gas purging stream ("Purge Gas" and dashed lines in FIG. 1) via Pump C through the pressure reactor to the precipitation reactor after the pressure reactor has been depressurized, or, optionally, some or all of the residual gases can be released to the atmosphere ("Waste Gas"). Any ammonia, carbon dioxide, or water vapor retained in the pressure reactor 4 can be supplemented by the introduction of ammonia, carbon dioxide, or water vapor into the influent gas stream to the precipitation reactor 5.

The gases entering the precipitation reactor 5 will undergo an exothermic reaction to produce ammonium bicarbonate/carbonate-based on the molar ratios of ammonia, carbon dioxide, and water vapor. The precipitation reactor 5 must be cooled sufficiently to remove the excess heat produced during the exothermic reaction. The heat can be removed through any of a variety of means including a heat pump chiller system. The precipitated ammonium bicarbonate is removed by Pump B or conveyor from the precipitation reactor 5 optionally to a storage vessel 6 where it is maintained for addition to the biomass stream. Any losses of ammonium bicarbonate/carbonate can be replenished by adding the required quantities to the ABC storage vessel 6. Alternatively, the precipitated ammonium bicarbonate/carbonate may be directly recycled to the influent biomass, bypassing storage.

Figure 2:
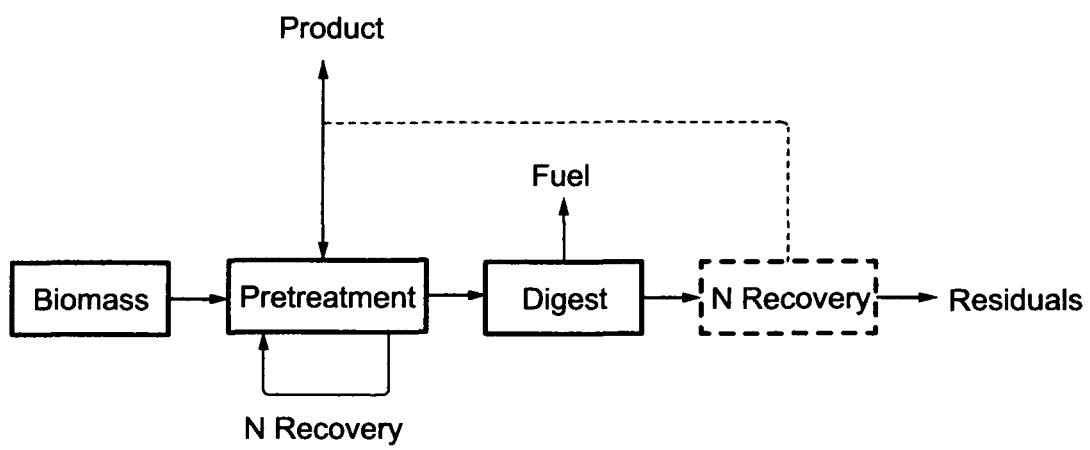
FIG. 2 is a schematic diagram of the ABFX pretreatment process ("Pretreatment") incorporated within a high solids, anaerobic digestion of a lignocellulosic substrate to thereby increase biogas fuel production.

The ABFX pretreatment process can be incorporated into a variety of renewable energy processes. FIG. 2 presents a first example of such an incorporation. A high solids, lignocellulose substrate ("Biomass") is subjected to the above-described ABFX pretreatment process ("Pretreatment"). The resulting pretreated substrate is then anaerobically digested ("Digest"), thereby producing "Fuel"—e.g., biogas produced by digestive fermentation. The pretreatment process, as depicted in FIG. 2, includes the nitrogen recovery ("N Recovery") in the form of ammonium bicarbonate/carbonate that is depicted by dashed lines. Any residual gases after anaerobic digestion may also optionally be subjected to similar N Recovery, as depicted by dashed lines in FIG. 2 to form a "Product"—e.g., ammonium bicarbonate/carbonate.

Figure 3:
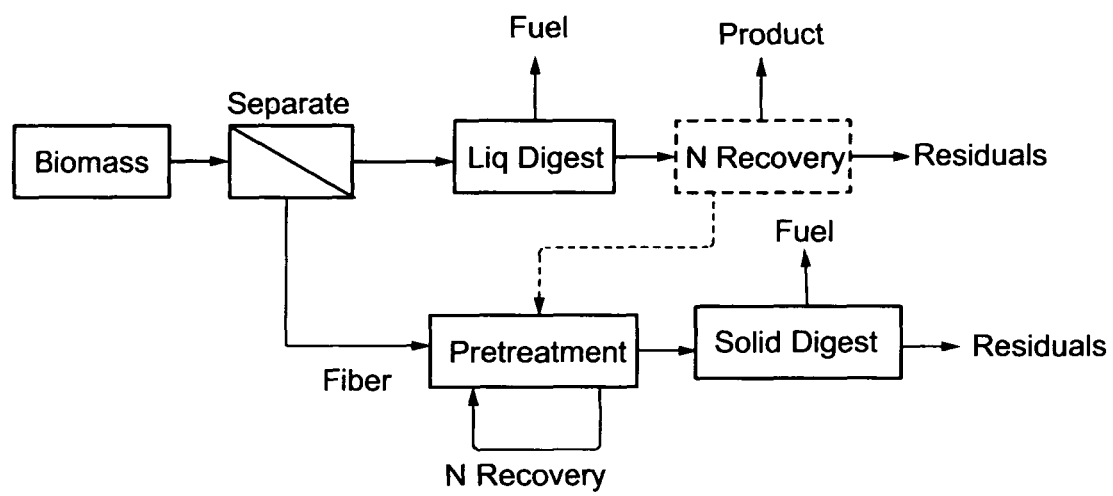
FIG. 3 is a schematic diagram of anaerobic digestion of a substrate, wherein the ABFX pretreatment process ("Pretreatment") is applied to fiber that has been separated from the substrate, and the pretreated fiber is then aerobically digested ("Solid Digest"); the liquid slurry is separately digested with optional nitrogen recovery and reuse in the process as indicated by the dashed lines.

FIG. 3 presents a second example of incorporation of ABFX pretreatment into a renewable energy process. A substrate, such as a lignocellulose biomass, undergoes separation ("Separate") into fiber and a fiber-deficient, liquid slurry. Such separation can be performed, for example, by conveying the substrate over an inclined mesh screen, whereby the fiber is retained above the screen and the liquid slurry collects below the screen. The fiber is pretreated by the ABFX pretreatment process ("Pretreatment") and the resulting pretreated fiber is then anaerobically digested ("Solid Digest") to yield fuel and residuals. The liquid slurry is anaerobically digested separately to yield fuel—e.g., biogas. The residual gases from the anaerobic digestion, principally including ammonia, carbon dioxide, and water vapor, optionally may undergo N Recovery in the above-stated manner, as indicated by the dashed lines in FIG. 3.

Figure 4:
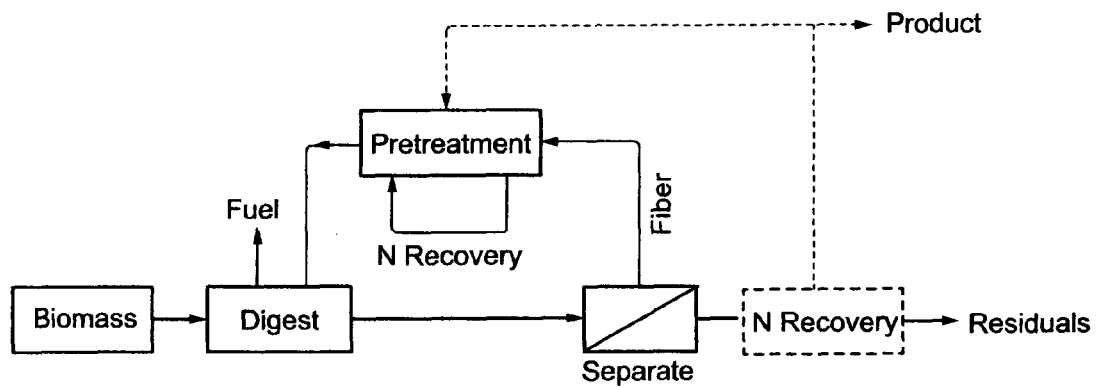
FIG. 4 is a schematic diagram of the ABFX pretreatment process applied to fiber that has been separated from a digested substrate slurry; the resulting pretreated fiber is then re-digested to thereby increase biogas yield ("Fuel").

FIG. 4 presents a third example of incorporation of ABFX pretreatment into a renewable energy process. A biomass substrate, such as a lignocellulosic substrate, undergoes anaerobic digestion ("Digest") thereby yielding "Fuel" (e.g., biogas) and a residual, fibrous slurry. The residual fibrous slurry undergoes separation ("Separate") into a fiber-deficient, liquid slurry and separated fiber ("Fiber"). The separated fiber is then subjected to ABFX pretreatment ("Pretreatment") and the resulting pretreated fiber then recycled through another round of anaerobic digestion "(Digest"). Optionally, as indicated by the dashed lines in FIG. 4, the fiber-deficient, liquid slurry undergoes N Recovery, thereby providing additional ammonium bicarbonate/carbonate to the ABFX pretreatment process and/or some or all of the ammonium bicarbonate/carbonate, which has commercial value, can be sequestered as an end product of the overall process.

Figure 5:
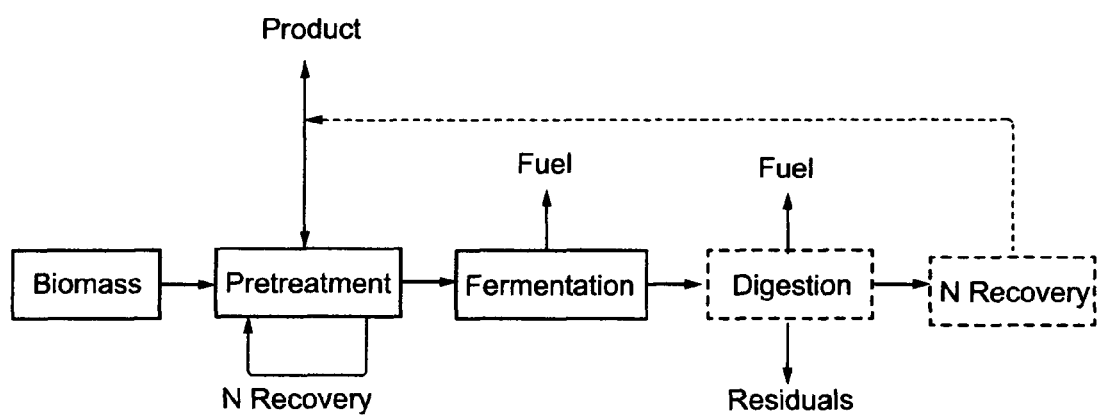
FIG. 5 is a schematic diagram of the ABFX pretreatment process ("Pretreatment") incorporated into the production of liquid fuels; the substrate first undergoes pretreatment as presented in FIG. 1, followed by fermentation for the production of liquid fuels. The residual slurry may be digested, followed by nitrogen recovery for use in the pretreatment process.

FIG. 5 presents a fourth example of incorporation of ABFX pretreatment into a renewable energy process. The substrate, which can be a ligocullulose substrate, undergoes ABFX pretreatment, as that pretreatment is presented in FIG. 1. The pretreated substrate undergoes fermentation ("Fermentation") thereby yielding liquid "Fuel" (e.g., ethanol) and a residual slurry. As indicated by the dashed lines in FIG. 5, the residual slurry may optionally be digested ("Digestion") to produce additional fuel and "Residuals." Gases, including ammonia, carbon dioxide and water vapor, remaining after digestion of the residual slurry can optionally undergo N Recovery and the resulting ammonium bicarbonate/carbonate can be recycled through another round of ABFX pretreatment ("Pretreatment") or some or all of the resulting ammonium bicarbonate/carbonate can be sequestered as an end product of the overall process.

Although specific embodiments of the invention have been illustrated and described herein, it will be appreciated by those of ordinary skill in the art that modifications and changes in the apparatus and methods set forth above will be possible without departing from the spirit and scope of the invention. For example, a variety of nitrogen-containing compounds can be used in the ABFX process, provided that, for present purposes, the term "nitrogen-containing compounds" shall mean only chemical compounds that contain nitrogen, have a decomposition or melting point in the range 35 to 80 degrees C., and decompose to yield ammonia bicarbonate and/or ammonia carbonate, as well as carbon dioxide and water vapor, when used in the ABFX process as described herein. They include, for instance, and without limitation, ammonium bicarbonate ($NH_4CO_3$), ammonium carbonate (($NH_4)_2CO_3$, ammonium carbamate ($NH_2COONH_4$). The most advantageous chemical compound or compounds are those that have the lowest melting or decomposition points. Of those listed hereinabove, ammonium bicarbonate has the lowest melting point at 41.9° C., followed by ammonium carbamate at 58° C. and ammonium carbamate at 59.61° C. Urea has a significantly higher melting point at 133° C., and thus is not recommended for use in the ABFX process, but many of the low-melting point, nitrogen-containing compounds can be used. Accordingly, it is intended that the following claims be interpreted to embrace all such modifications and changes as will be apparent to one having ordinary skill in this technology.

REFERENCES

Gouveia, L. (2011). *Microalgae as a feedstock for biofuels*, Springer Lisboa.
Kumar, D., and Murthy, G. S. (2011). "Pretreatments and enzymatic hydrolysis of grass straws for ethanol production in the Pacific Northwest U.S." *Biological Engineering*, 3(2), 13.
O'Connor, J. J. (1971). "Exploding of ammonia impregnated wood chips." USPTO, ed., 12.
Dale, B. E. (1986). "Method for increasing the reactivity and digestibility of cellulose with ammonia." Colorado State University Research Foundation, USA.
Norman, R. J., Gilmour, J. T., and GALE, P. M. (1987). "Transformations of organic matter solubilized by anhydrous ammonia." *Transactions ASAE*.
Dale, B. E., Bals, B., and Balan, V. (2009). "Separation of proteins from grasses integrated with ammonia fiber explosion (AFEX) pretreatment and cellulose hydrolysis." USPTO, ed., 12.
Zhang, Y. H. (2009). "Method and apparatus for lignocellulosic pretreatment using a super-cellulose-solvent and highly volatile solvents." USPTO, ed.
Geros, D. G. (2010). "Method for the production of concentrated alcohol from fermentation broths." *USPTO*.
Kreisler, K. E. (2010). "Methods for enhanced processing of biomass using flash dessication and/or mechanical hydrodynamic cavitation." USPTO, ed.
Parekh, S. (2010). "Compositions and Methods for Fermentation of Biomass." USPTO, ed.
Sudhakaran, and Samuel, D. (2010). "Process for separating biomass components."
Mosier, N., Wyman, C., Dale, B., Elander, R., Lee, Y. Y., Holtzapple, M., and Ladisch, M. (2005). "Features of promising technologies for pretreatment of lignocellulosic biomass." *Bioresour. Technol*, 96(6), 673-686.
Teymouri, F., Laureano-Perez, L., Alizadeh, H., and Dale, B. E. (2005.). "Optimization of the ammonia fiber explosion (AFEX) treatment parameters for enzymatic hydrolysis of corn stover." *Bioresour Technol*, 96(18), 12.
Sousa, L. D. C., Chundawat, S. P., and, V. B., and Dale, B. E. (2009). "Cradle-to-grave assessment of existing lignocellulose pretreatment technologies." *Biotechnology*, 20(1), 9.

What is claimed is:

1. A method for pretreating a biomass to improve the susceptibility of the biomass to hydrolysis, comprising the steps of:
    (a) blending and/or mixing the biomass with one or more solid, nitrogen-containing compounds having a decomposition or melting point in the range 35 to 80 degrees C. within a mixing/blending vessel at any desired feed ratio to produce a blended, mixed feedstock;
    (b) transferring said blended, mixed feedstock into a pressure reactor;
    (c) sealing the pressure reactor;
    (d) heating the feedstock within the pressure reactor to a temperature sufficient to decompose said nitrogen-containing compounds into gaseous ammonia, carbon dioxide and water vapor, thereby increasing pressure within the reactor;
    (e) holding the feedstock within the pressure reactor at a desired pressure and temperature for a desired time interval;
    (f) unsealing the pressure reactor by releasing the carbon dioxide, water vapor, and ammonia gases therefrom;
    (g) conducting the released carbon dioxide, water vapor and ammonia gases from the pressure reactor into the interior of a precipitation reactor, thereby leaving residual contents in the pressure reactor;
    (h) cooling said released carbon dioxide, water vapor and ammonia in the precipitation reactor sufficiently to precipitate ammonium bicarbonate/carbonate therein;
    (i) conducting some or all of the precipitated ammonium bicarbonate/carbonate away from the precipitation reactor; and
    (j) removing the residual contents of the pressure reactor from the pressure reactor.

2. The method of claim 1, wherein said nitrogen-containing compounds comprise one or more of ammonia bicarbonate, ammonia carbonate, and ammonia carbamate.

3. The method of claim 1, wherein said mixing/blending vessel and said pressure reactor are one and the same.

4. The method of claim 2, further comprising blending and/or mixing with the biomass some or all of the precipitated ammonium bicarbonate/carbonate to produce said blended, mixed feedstock.

5. The method of claim 4, further comprising, after step (f), purging any residual gases within the pressure reactor.

6. The method of claim 5, wherein, after step (f), gases within the precipitation reactor are conducted to, and pumped through, the pressure reactor to purge residual gases out of the pressure reactor.

7. The method of claim 1, wherein a heat pump provides the heat for heating the feedstock in step (d) and provides the cooling in step (h).

8. The method of claim 4, wherein the method is carried out as a continuous process.

9. The method of claim 4, wherein the method is carried out as a batch process.

10. The method of claim 4, further comprising adding makeup ammonium bicarbonate and/or ammonium carbonate to the biomass, as needed.

11. The method of claim 1, further comprising macerating, ensilaging and/or drying the biomass prior to step (a).

12. The method of claim 4, wherein said mixing/blending vessel is a biomass conveyor.

13. The method of claim 4, wherein said mixing/blending vessel is the influent hopper of a solids feed pump.

14. The method of claim 1, wherein the biomass is a high solids biomass.

15. A method for digestion of a high solids, lignocellulosic biomass, comprising the steps of
   (a) pretreating said biomass according to the method of claim 2 to produce a pretreated biomass; and
   (b) anaerobically digesting or fermenting the pretreated biomass produced in step (a) in a digester, thereby producing a fuel.

16. The method of claim 15, wherein said fuel comprises biogas.

17. The method of claim 15, wherein said fuel comprises ethanol.

18. The method of claim 15, further comprising conducting any residual carbon dioxide, water vapor and ammonia gases from the digester into the interior of said precipitation reactor and precipitating said gases therein to ammonium bicarbonate/carbonate.

19. A method for digestion of a high solids, lignocellulosic biomass comprised of fiber and a liquid slurry, including the steps of
   (a) separating the fiber from the liquid slurry;
   (b) pretreating the fiber according to the method of claim 1 to produce a pretreated fiber; and
   (c) anaerobically digesting the pretreated fiber produced in step (b) in a digester, thereby producing a first fuel.

20. The method of claim 19, further comprising digesting the liquid slurry in a digester to produce a second fuel.

21. The method of claim 20, wherein the first fuel comprises biogas and the second fuel comprises a liquid or gaseous fuel.

22. The method of claim 19, further comprising
   (a) conducting any residual ammonia, carbon dioxide and water vapor in said digester from said digester into the interior of a precipitation reactor;
   (b) cooling said residual carbon dioxide, water vapor and ammonia in the precipitation reactor sufficiently to precipitate ammonium bicarbonate/carbonate therein;
   (c) conducting some or all of the precipitated ammonium bicarbonate/carbonate away from the precipitation reactor.

23. A method for digestion of a high solids, lignocellulosic biomass comprised of fiber and a liquid slurry, comprising the steps of
   (a) anaerobically digesting the biomass to produce a fuel and a residual slurry;
   (b) separating the residual, fibrous slurry into fiber and a liquid slurry; and
   (c) pretreating said fiber according to the method of claim 2 to produce pretreated fiber and precipitate ammonium bicarbonate/carbonate.

24. The method of claim 23, further comprising using some or all of the ammonia bicarbonate/carbonate produced in step (c) of claim 23 to perform step (a) of claim 1.

25. The method of claim 24, further comprising N recovery by the steps of
   (a) conducting any residual ammonia, carbon dioxide and water vapor in said digester into the interior of a precipitation reactor;
   (b) cooling said residual carbon dioxide, water vapor and ammonia in the precipitation reactor sufficiently to precipitate ammonium bicarbonate/carbonate therein; and
   (c) conducting some or all of the precipitated ammonium bicarbonate/carbonate away from the precipitation reactor.

26. A method for production of liquid fuel from lignocellulosic biomass, comprising the steps of
   (a) pretreating the biomass according to claim 1 to produce a pretreated biomass; and
   (b) fermenting said pretreated biomass to produce a first liquid fuel and a residual slurry.

27. The method of claim 26, further comprising anaerobically digesting said residual slurry in a digester to produce a second fuel and residuals.

28. The method of claim 27, comprising N recovery by the steps of
   (a) conducting any residual ammonia, carbon dioxide and water vapor in said digester from said digester into the interior of a precipitation reactor;
   (b) cooling said residual carbon dioxide, water vapor and ammonia in the precipitation reactor sufficiently to precipitate ammonium bicarbonate/carbonate; and
   (c) conducting some or all of the precipitated ammonium bicarbonate/carbonate away from the precipitation reactor.

* * * * *